(12) United States Patent
Williams (10) Patent No.: US 11,406,391 B2
(45) Date of Patent: *Aug. 9, 2022

(54) ADAPTER ASSEMBLY FOR SURGICAL DEVICES

(71) Applicant: Covidien LP, Mansfield, MA (US)

(72) Inventor: Justin Williams, Southbury, CT (US)

(73) Assignee: Covidien LP, Mansfield, MA (US)

( * ) Notice: Subject to any disclaimer, the term of this patent is extended or adjusted under 35 U.S.C. 154(b) by 408 days.

This patent is subject to a terminal disclaimer.

(21) Appl. No.: 16/531,207

(22) Filed: Aug. 5, 2019

(65) Prior Publication Data

US 2019/0350586 A1    Nov. 21, 2019

Related U.S. Application Data

(63) Continuation of application No. 14/882,550, filed on Oct. 14, 2015, now Pat. No. 10,413,298.

(51) Int. Cl.
*A61B 17/115* (2006.01)
*A61B 17/34* (2006.01)
*A61B 17/00* (2006.01)

(52) U.S. Cl.
CPC .......... *A61B 17/1155* (2013.01); *A61B 17/34* (2013.01); *A61B 2017/0046* (2013.01); *A61B 2017/00367* (2013.01); *A61B 2017/00398* (2013.01); *A61B 2017/00477* (2013.01)

(58) Field of Classification Search
CPC ............... A61B 17/1155; A61B 17/34; A61B 2017/00367; A61B 2017/00398; A61B 2017/0046; A61B 2017/00477
See application file for complete search history.

(56) References Cited

U.S. PATENT DOCUMENTS

| 2,777,340 A | 1/1957 | Hettwer et al. |
| 2,957,353 A | 10/1960 | Babacz |
| 3,111,328 A | 11/1963 | Di Rito et al. |
| 3,695,058 A | 10/1972 | Keith, Jr. |
| 3,734,515 A | 5/1973 | Dudek |
| 3,759,336 A | 9/1973 | Marcovitz et al. |
| 4,162,399 A | 7/1979 | Hudson |
| 4,606,343 A | 8/1986 | Conta et al. |
| 4,705,038 A | 11/1987 | Sjostrom et al. |
| 4,722,685 A | 2/1988 | de Estrada et al. |

(Continued)

FOREIGN PATENT DOCUMENTS

| CA | 2451558 A1 | 1/2003 |
| CA | 2824590 A1 | 4/2014 |

(Continued)

OTHER PUBLICATIONS

Extended European Search Report corresponding to International Application No. EP 14 18 4882.0 dated May 12, 2015.

(Continued)

*Primary Examiner* — David B. Thomas
(74) *Attorney, Agent, or Firm* — Carter, DeLuca & Farrell LLP (57) ABSTRACT

An adapter assembly for connecting an end effector to a handle assembly includes first, second, and third drive assemblies configured for converting rotational motion from the handle assembly to linear motion for performing first, second, and third functions.

17 Claims, 10 Drawing Sheets

(56) References Cited

U.S. PATENT DOCUMENTS

| | | | |
|---|---|---|---|
| 4,823,807 A | 4/1989 | Russell et al. |
| 4,874,181 A | 10/1989 | Hsu |
| 5,129,118 A | 7/1992 | Walmesley |
| 5,129,570 A | 7/1992 | Schulze et al. |
| 5,152,744 A | 10/1992 | Krause et al. |
| 5,301,061 A | 4/1994 | Nakada et al. |
| 5,312,023 A | 5/1994 | Green et al. |
| 5,326,013 A | 7/1994 | Green et al. |
| 5,350,355 A | 9/1994 | Sklar |
| 5,383,874 A | 1/1995 | Jackson et al. |
| 5,383,880 A | 1/1995 | Hooven |
| 5,389,098 A | 2/1995 | Tsuruta et al. |
| 5,395,033 A | 3/1995 | Byrne et al. |
| 5,400,267 A | 3/1995 | Denen et al. |
| 5,411,508 A | 5/1995 | Bessler et al. |
| 5,413,267 A | 5/1995 | Solyntjes et al. |
| 5,427,087 A | 6/1995 | Ito et al. |
| 5,433,721 A | 7/1995 | Hooven et al. |
| 5,467,911 A | 11/1995 | Tsuruta et al. |
| 5,476,379 A | 12/1995 | Disel |
| 5,487,499 A | 1/1996 | Sorrentino et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,535,934 A | 7/1996 | Boiarski et al. |
| 5,535,937 A | 7/1996 | Boiarski et al. |
| 5,540,375 A | 7/1996 | Bolanos et al. |
| 5,540,706 A | 7/1996 | Aust et al. |
| 5,542,594 A | 8/1996 | McKean et al. |
| 5,549,637 A | 8/1996 | Crainich |
| 5,553,675 A | 9/1996 | Pitzen et al. |
| 5,562,239 A | 10/1996 | Boiarski et al. |
| 5,564,615 A | 10/1996 | Bishop et al. |
| 5,609,560 A | 3/1997 | Ichikawa et al. |
| 5,626,587 A | 5/1997 | Bishop et al. |
| 5,632,432 A | 5/1997 | Schulze et al. |
| 5,645,209 A | 7/1997 | Green et al. |
| 5,647,526 A | 7/1997 | Green et al. |
| 5,653,374 A | 8/1997 | Young et al. |
| 5,658,300 A | 8/1997 | Bito et al. |
| 5,662,662 A | 9/1997 | Bishop et al. |
| 5,667,517 A | 9/1997 | Hooven |
| 5,693,042 A | 12/1997 | Boiarski et al. |
| 5,704,534 A | 1/1998 | Huitema et al. |
| 5,713,505 A | 2/1998 | Huitema |
| 5,762,603 A | 6/1998 | Thompson |
| 5,779,130 A | 7/1998 | Alesi et al. |
| 5,782,396 A | 7/1998 | Mastri et al. |
| 5,782,397 A | 7/1998 | Koukline |
| 5,792,573 A | 8/1998 | Pitzen et al. |
| 5,797,536 A | 8/1998 | Smith et al. |
| 5,820,009 A | 10/1998 | Melling et al. |
| 5,863,159 A | 1/1999 | Lasko |
| 5,908,427 A | 6/1999 | McKean et al. |
| 5,954,259 A | 9/1999 | Viola et al. |
| 5,964,774 A | 10/1999 | McKean et al. |
| 5,993,454 A | 11/1999 | Longo |
| 6,010,054 A | 1/2000 | Johnson et al. |
| 6,017,354 A | 1/2000 | Culp et al. |
| 6,032,849 A | 3/2000 | Mastri et al. |
| 6,045,560 A | 4/2000 | McKean et al. |
| 6,090,123 A | 7/2000 | Culp et al. |
| 6,126,651 A | 10/2000 | Mayer |
| 6,129,547 A | 10/2000 | Cise et al. |
| 6,165,169 A | 12/2000 | Panescu et al. |
| 6,239,732 B1 | 5/2001 | Cusey |
| 6,241,139 B1 | 6/2001 | Milliman et al. |
| 6,264,086 B1 | 7/2001 | McGuckin, Jr. |
| 6,264,087 B1 | 7/2001 | Whitman |
| 6,302,311 B1 | 10/2001 | Adams et al. |
| 6,315,184 B1 | 11/2001 | Whitman |
| 6,321,855 B1 | 11/2001 | Barnes |
| 6,329,778 B1 | 12/2001 | Culp et al. |
| 6,343,731 B1 | 2/2002 | Adams et al. |
| 6,348,061 B1 | 2/2002 | Whitman |
| 6,368,324 B1 | 4/2002 | Dinger et al. |
| 6,371,909 B1 | 4/2002 | Hoeg et al. |
| 6,434,507 B1 | 8/2002 | Clayton et al. |
| 6,443,973 B1 | 9/2002 | Whitman |
| 6,461,372 B1 | 10/2002 | Jensen et al. |
| 6,488,197 B1 | 12/2002 | Whitman |
| 6,491,201 B1 | 12/2002 | Whitman |
| 6,533,157 B1 | 3/2003 | Whitman |
| 6,537,280 B2 | 3/2003 | Dinger et al. |
| 6,610,066 B2 | 8/2003 | Dinger et al. |
| 6,611,793 B1 | 8/2003 | Burnside et al. |
| 6,645,218 B1 | 11/2003 | Cassidy et al. |
| 6,654,999 B2 | 12/2003 | Stoddard et al. |
| 6,698,643 B2 | 3/2004 | Whitman |
| 6,699,177 B1 | 3/2004 | Wang et al. |
| 6,716,233 B1 | 4/2004 | Whitman |
| 6,743,240 B2 | 6/2004 | Smith et al. |
| 6,783,533 B2 | 8/2004 | Green et al. |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,860,892 B1 | 3/2005 | Tanaka et al. |
| 6,899,538 B2 | 5/2005 | Matoba |
| 6,905,057 B2 | 6/2005 | Swayze et al. |
| 6,959,852 B2 | 11/2005 | Shelton, IV et al. |
| 6,964,363 B2 | 11/2005 | Wales et al. |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 7,032,798 B2 | 4/2006 | Whitman et al. |
| RE39,152 E | 6/2006 | Aust et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,111,769 B2 | 9/2006 | Wales et al. |
| 7,122,029 B2 | 10/2006 | Koop et al. |
| 7,140,528 B2 | 11/2006 | Shelton, IV |
| 7,141,049 B2 | 11/2006 | Stern et al. |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,172,104 B2 | 2/2007 | Scirica et al. |
| 7,225,964 B2 | 6/2007 | Mastri et al. |
| 7,238,021 B1 | 7/2007 | Johnson |
| 7,246,734 B2 | 7/2007 | Shelton, IV |
| 7,252,660 B2 | 8/2007 | Kunz |
| 7,328,828 B2 | 2/2008 | Ortiz et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,637,409 B2 | 12/2009 | Marczyk |
| 7,641,093 B2 | 1/2010 | Doll et al. |

(56) References Cited

U.S. PATENT DOCUMENTS

| | | |
|---|---|---|
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,870,989 B2 | 1/2011 | Viola et al. |
| 7,900,805 B2 | 3/2011 | Shelton, IV et al. |
| 7,905,897 B2 | 3/2011 | Whitman et al. |
| 7,918,230 B2 | 4/2011 | Whitman et al. |
| 7,922,061 B2 | 4/2011 | Shelton, IV et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 8,011,550 B2 | 9/2011 | Aranyi et al. |
| 8,016,178 B2 | 9/2011 | Olson et al. |
| 8,016,855 B2 | 9/2011 | Whitman et al. |
| 8,020,743 B2 | 9/2011 | Shelton, IV |
| 8,025,199 B2 | 9/2011 | Whitman et al. |
| 8,035,487 B2 | 10/2011 | Malackowski |
| 8,052,024 B2 | 11/2011 | Viola et al. |
| 8,114,118 B2 | 2/2012 | Knodel et al. |
| 8,127,975 B2 | 3/2012 | Olson et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,272,554 B2 | 9/2012 | Whitman et al. |
| 8,292,150 B2 | 10/2012 | Bryant |
| 8,292,888 B2 | 10/2012 | Whitman |
| 8,342,379 B2 | 1/2013 | Whitman et al. |
| 8,348,130 B2 | 1/2013 | Shah et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,403,926 B2 | 3/2013 | Nobis et al. |
| 8,418,904 B2 | 4/2013 | Wenchell et al. |
| 8,424,739 B2 | 4/2013 | Racenet et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,523,043 B2 | 9/2013 | Ullrich et al. |
| 8,551,076 B2 | 10/2013 | Duval et al. |
| 8,561,871 B2 | 10/2013 | Rajappa et al. |
| 8,561,874 B2 | 10/2013 | Scirica |
| 8,602,287 B2 | 12/2013 | Yates et al. |
| 8,623,000 B2 | 1/2014 | Humayun et al. |
| 8,627,995 B2 | 1/2014 | Smith et al. |
| 8,632,463 B2 | 1/2014 | Drinan et al. |
| 8,636,766 B2 | 1/2014 | Milliman et al. |
| 8,647,258 B2 | 2/2014 | Aranyi et al. |
| 8,652,121 B2 | 2/2014 | Quick et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,715,306 B2 | 5/2014 | Faller et al. |
| 8,758,391 B2 | 6/2014 | Swayze et al. |
| 8,806,973 B2 | 8/2014 | Ross et al. |
| 8,808,311 B2 | 8/2014 | Heinrich et al. |
| 8,820,605 B2 | 9/2014 | Shelton, IV |
| 8,851,355 B2 | 10/2014 | Aranyi et al. |
| 8,858,571 B2 | 10/2014 | Shelton, IV et al. |
| 8,875,972 B2 | 11/2014 | Weisenburgh, II et al. |
| 8,888,762 B2 | 11/2014 | Whitman |
| 8,893,946 B2 | 11/2014 | Boudreaux et al. |
| 8,899,462 B2 | 12/2014 | Kostrzewski et al. |
| 8,905,289 B2 | 12/2014 | Patel et al. |
| 8,919,630 B2 | 12/2014 | Milliman |
| 8,931,680 B2 | 1/2015 | Milliman |
| 8,939,344 B2 | 1/2015 | Olson et al. |
| 8,950,646 B2 | 2/2015 | Viola |
| 8,960,519 B2 | 2/2015 | Whitman et al. |
| 8,961,396 B2 | 2/2015 | Azarbarzin et al. |
| 8,967,443 B2 | 3/2015 | McCuen |
| 8,968,276 B2 | 3/2015 | Zemlok et al. |
| 8,968,337 B2 | 3/2015 | Whitfield et al. |
| 8,992,422 B2 | 3/2015 | Spivey et al. |
| 9,016,545 B2 | 4/2015 | Aranyi et al. |
| 9,023,014 B2 | 5/2015 | Chowaniec et al. |
| 9,033,868 B2 | 5/2015 | Whitman et al. |
| 9,055,943 B2 | 6/2015 | Zemlok et al. |
| 9,064,653 B2 | 6/2015 | Prest et al. |
| 9,072,515 B2 | 7/2015 | Hall et al. |
| 9,113,847 B2 | 8/2015 | Whitman et al. |
| 9,113,875 B2 | 8/2015 | Viola et al. |
| 9,113,876 B2 | 8/2015 | Zemlok et al. |
| 9,113,899 B2 | 8/2015 | Garrison et al. |
| 9,216,013 B2 | 12/2015 | Scirica et al. |
| 9,282,961 B2 | 3/2016 | Whitman et al. |
| 9,282,963 B2 | 3/2016 | Bryant |
| 9,295,522 B2 | 3/2016 | Kostrzewski |
| 9,307,986 B2 | 4/2016 | Hall et al. |
| 10,413,298 B2 * | 9/2019 | Williams ............ A61B 17/1155 |
| 2001/0031975 A1 | 10/2001 | Whitman et al. |
| 2002/0049454 A1 | 4/2002 | Whitman et al. |
| 2002/0165541 A1 | 11/2002 | Whitman |
| 2003/0038938 A1 | 2/2003 | Jung et al. |
| 2003/0165794 A1 | 9/2003 | Matoba |
| 2004/0111012 A1 | 6/2004 | Whitman |
| 2004/0133189 A1 | 7/2004 | Sakurai |
| 2004/0153124 A1 | 8/2004 | Whitman |
| 2004/0176751 A1 | 9/2004 | Weitzner et al. |
| 2004/0193146 A1 | 9/2004 | Lee et al. |
| 2005/0125027 A1 | 6/2005 | Knodel et al. |
| 2005/0131442 A1 | 6/2005 | Yachia et al. |
| 2006/0142656 A1 | 6/2006 | Malackowski et al. |
| 2006/0142740 A1 | 6/2006 | Sherman et al. |
| 2006/0142744 A1 | 6/2006 | Boutoussov |
| 2006/0259073 A1 | 11/2006 | Miyamoto et al. |
| 2006/0278680 A1 | 12/2006 | Viola et al. |
| 2006/0284730 A1 | 12/2006 | Schmid et al. |
| 2007/0023476 A1 | 2/2007 | Whitman et al. |
| 2007/0023477 A1 | 2/2007 | Whitman et al. |
| 2007/0029363 A1 | 2/2007 | Popov |
| 2007/0084897 A1 | 4/2007 | Shelton et al. |
| 2007/0102472 A1 | 5/2007 | Shelton |
| 2007/0152014 A1 | 7/2007 | Gillum et al. |
| 2007/0175947 A1 | 8/2007 | Ortiz et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |

(56) References Cited

U.S. PATENT DOCUMENTS

| | | |
|---|---|---|
| 2007/0175955 A1 | 8/2007 | Shelton et al. |
| 2007/0175961 A1 | 8/2007 | Shelton et al. |
| 2007/0270784 A1 | 11/2007 | Smith et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0058801 A1 | 3/2008 | Taylor et al. |
| 2008/0109012 A1 | 5/2008 | Falco et al. |
| 2008/0110958 A1 | 5/2008 | McKenna et al. |
| 2008/0147089 A1 | 6/2008 | Loh et al. |
| 2008/0167736 A1 | 7/2008 | Swayze et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237296 A1 | 10/2008 | Boudreaux et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0308603 A1 | 12/2008 | Shelton et al. |
| 2009/0012533 A1 | 1/2009 | Barbagli |
| 2009/0090763 A1 | 4/2009 | Zemlok et al. |
| 2009/0099876 A1 | 4/2009 | Whitman |
| 2009/0138006 A1 | 5/2009 | Bales et al. |
| 2009/0171147 A1 | 7/2009 | Lee et al. |
| 2009/0182193 A1 | 7/2009 | Whitman et al. |
| 2009/0209990 A1 | 8/2009 | Yates et al. |
| 2009/0254094 A1 | 10/2009 | Knapp et al. |
| 2009/0299141 A1 | 12/2009 | Downey et al. |
| 2010/0023022 A1 | 1/2010 | Zeiner et al. |
| 2010/0069942 A1 | 3/2010 | Shelton, IV |
| 2010/0193568 A1 | 8/2010 | Scheib et al. |
| 2010/0211053 A1 | 8/2010 | Ross et al. |
| 2010/0225073 A1 | 9/2010 | Porter et al. |
| 2011/0071508 A1 | 3/2011 | Duval et al. |
| 2011/0077673 A1 | 3/2011 | Grubac et al. |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0155786 A1 | 6/2011 | Shelton, IV |
| 2011/0172648 A1 | 7/2011 | Jeong |
| 2011/0174099 A1 | 7/2011 | Ross et al. |
| 2011/0184245 A1 | 7/2011 | Xia et al. |
| 2011/0204119 A1 | 8/2011 | McCuen |
| 2011/0218522 A1 | 9/2011 | Whitman |
| 2011/0276057 A1 | 11/2011 | Conlon et al. |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0074199 A1 | 3/2012 | Olson et al. |
| 2012/0089131 A1 | 4/2012 | Zemlok et al. |
| 2012/0104071 A1 | 5/2012 | Bryant |
| 2012/0116368 A1 | 5/2012 | Viola |
| 2012/0143002 A1 | 6/2012 | Aranyi et al. |
| 2012/0172924 A1 | 7/2012 | Allen, IV |
| 2012/0211542 A1 | 8/2012 | Racenet |
| 2012/0223121 A1 | 9/2012 | Viola et al. |
| 2012/0245428 A1 | 9/2012 | Smith et al. |
| 2012/0253329 A1 | 10/2012 | Zemlok et al. |
| 2012/0310220 A1 | 12/2012 | Malkowski et al. |
| 2012/0323226 A1 | 12/2012 | Chowaniec et al. |
| 2012/0330285 A1 | 12/2012 | Hartoumbekis et al. |
| 2013/0018361 A1 | 1/2013 | Bryant |
| 2013/0093149 A1 | 4/2013 | Saur et al. |
| 2013/0181035 A1 | 7/2013 | Milliman |
| 2013/0184704 A1 | 7/2013 | Beardsley et al. |
| 2013/0214025 A1 | 8/2013 | Zemlok et al. |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0025046 A1 | 1/2014 | Williams et al. |
| 2014/0110455 A1 | 4/2014 | Ingmanson et al. |
| 2014/0207125 A1 | 7/2014 | Applegate et al. |
| 2014/0207182 A1 | 7/2014 | Zergiebel et al. |
| 2014/0207185 A1 | 7/2014 | Goble et al. |
| 2014/0236173 A1 | 8/2014 | Scirica et al. |
| 2014/0236174 A1 | 8/2014 | Williams et al. |
| 2014/0276932 A1 | 9/2014 | Williams et al. |
| 2014/0299647 A1 | 10/2014 | Scirica et al. |
| 2014/0303668 A1 | 10/2014 | Nicholas et al. |
| 2014/0358129 A1 | 12/2014 | Zergiebel et al. |
| 2014/0361068 A1 | 12/2014 | Aranyi et al. |
| 2014/0365235 A1 | 12/2014 | DeBoer et al. |
| 2014/0373652 A1 | 12/2014 | Zergiebel et al. |
| 2015/0014392 A1 | 1/2015 | Williams et al. |
| 2015/0048144 A1 | 2/2015 | Whitman |
| 2015/0076205 A1 | 3/2015 | Zergiebel |
| 2015/0080912 A1 | 3/2015 | Sapre |
| 2015/0112381 A1 | 4/2015 | Richard |
| 2015/0122870 A1 | 5/2015 | Zemlok et al. |
| 2015/0133224 A1 | 5/2015 | Whitman et al. |
| 2015/0133957 A1 | 5/2015 | Kostrzewski |
| 2015/0150547 A1 | 6/2015 | Ingmanson et al. |
| 2015/0150574 A1 | 6/2015 | Richard et al. |
| 2015/0157320 A1 | 6/2015 | Zergiebel et al. |
| 2015/0157321 A1 | 6/2015 | Zergiebel et al. |
| 2015/0164502 A1 | 6/2015 | Richard et al. |
| 2015/0201931 A1 | 7/2015 | Zergiebel et al. |
| 2015/0272577 A1 | 10/2015 | Zemlok et al. |
| 2015/0297199 A1 | 10/2015 | Nicholas et al. |
| 2015/0303996 A1 | 10/2015 | Calderoni |
| 2015/0320420 A1 | 11/2015 | Penna et al. |
| 2015/0327850 A1 | 11/2015 | Kostrzewski |
| 2015/0342601 A1 | 12/2015 | Williams et al. |
| 2015/0342603 A1 | 12/2015 | Zergiebel et al. |
| 2015/0374366 A1 | 12/2015 | Zergiebel et al. |
| 2015/0374370 A1 | 12/2015 | Zergiebel et al. |
| 2015/0374371 A1 | 12/2015 | Richard et al. |
| 2015/0374372 A1 | 12/2015 | Zergiebel et al. |
| 2015/0374449 A1 | 12/2015 | Chowaniec et al. |
| 2015/0380187 A1 | 12/2015 | Zergiebel et al. |
| 2016/0095585 A1 | 4/2016 | Zergiebel et al. |
| 2016/0095596 A1 | 4/2016 | Scirica et al. |
| 2016/0106406 A1 | 4/2016 | Cabrera et al. |
| 2016/0113648 A1 | 4/2016 | Zergiebel et al. |
| 2016/0113649 A1 | 4/2016 | Zergiebel et al. |

FOREIGN PATENT DOCUMENTS

| | | |
|---|---|---|
| CN | 102247182 A | 11/2011 |
| DE | 102008053842 A1 | 5/2010 |
| EP | 0705571 A1 | 4/1996 |
| EP | 1769754 A1 | 4/2007 |
| EP | 2055243 A2 | 5/2009 |
| EP | 2316345 A1 | 5/2011 |
| EP | 2333509 A1 | 6/2011 |
| EP | 2668910 A2 | 12/2013 |
| ES | 2333509 A1 | 2/2010 |
| JP | 08038488 | 2/1996 |
| JP | 2005125075 A | 5/2005 |
| KR | 20120022521 A | 3/2012 |
| WO | 2011108840 A2 | 9/2011 |
| WO | 2012/040984 A1 | 4/2012 |

OTHER PUBLICATIONS

Canadian Office Action corresponding to International Application No. CA 2640399 dated May 7, 2015.

Japanese Office Action corresponding to International Application No. JP 2011-197365 dated Mar. 23, 2015.

(56) References Cited

OTHER PUBLICATIONS

Japanese Office Action corresponding to International Application No. JP 2011-084092 dated May 20, 2015.
Japanese Office Action corresponding to International Application No. JP 2014-148482 dated Jun. 2, 2015.
Extended European Search Report corresponding to International Application No. EP 14 18 9358.6 dated Jul. 8, 2015.
Extended European Search Report corresponding to International Application No. EP 14 19 6148.2 dated Apr. 23, 2015.
Partial European Search Report corresponding to International Application No. EP 14 19 6704.2 dated May 11, 2015.
Australian Office Action corresponding to International Application No. AU 2010241367 dated Aug. 20, 2015.
Partial European Search Report corresponding to International Application No. EP 14 19 9783.3 dated Sep. 3, 2015.
Extended European Search Report corresponding to International Application No. EP 15 16 9962.6 dated Sep. 14, 2015.
Extended European Search Report corresponding to International Application No. EP 15 15 1076.5 dated Apr. 22, 2015.
Japanese Office Action corresponding to International Application No. JP 2011-084092 dated Jan. 14, 2016.
Extended European Search Report corresponding to International Application No. EP 12 19 7970.2 dated Jan. 28, 2016.
Chinese Office Action corresponding to International Application No. CN 201210560638.1 dated Oct. 21, 2015.
European Office Action corresponding to International Application No. EP 14 15 9056.2 dated Oct. 26, 2015.
Australian Examination Report No. 1 corresponding to International Application No. AU 2015200153 dated Dec. 11, 2015.
Australian Examination Report No. 1 corresponding to International Application No. AU 2014204542 dated Jan. 7, 2016.
Chinese Office Action corresponding to International Application No. CN 201310125449.6 dated Feb. 3, 2016.
Extended European Search Report corresponding to International Application No. EP 15 19 0245.9 dated Jan. 28, 2016.
Extended European Search Report corresponding to International Application No. EP 15 16 7793.7 dated Apr. 5, 2016.
European Office Action corresponding to International Application No. EP 14 18 4882.0 dated Apr. 25, 2016.
Extended European Search Report corresponding to International Application No. EP 14 19 6704.2 dated Sep. 24, 2015.
International Search Report and Written Opinion corresponding to Int'l Appln. No. PCT/US2015/051837, dated Dec. 21, 2015.
Extended European Search Report corresponding to International Application No. EP 14 19 7563.1 dated Aug. 5, 2015.
Partial European Search Report corresponding to International Application No. EP 15 19 0643.5 dated Feb. 26, 2016.
Extended European Search Report corresponding to International Application No. EP 15 16 6899.3 dated Feb. 3, 2016.
Extended European Search Report corresponding to International Application No. EP 14 19 9783.3 dated Dec. 22, 2015.
Extended European Search Report corresponding to International Application No. EP 15 17 3807.7 dated Nov. 24, 2015.
Extended European Search Report corresponding to International Application No. EP 15 19 0760.7 dated Apr. 1, 2016.
Extended European Search Report corresponding to International Application No. EP 15 17 3803.6 dated Nov. 24, 2015.
Extended European Search Report corresponding to International Application No. EP 15 17 3804.4 dated Nov. 24, 2015.
Extended European Search Report corresponding to International Application No. EP 15 18 8539.9 dated Feb. 17, 2016.
Extended European Search Report corresponding to International Application No. EP 15 17 3910.9 dated Nov. 13, 2015.
European Office Action corresponding to International Application No. EP 14 15 2236.7 dated Aug. 11, 2015.
Extended European Search Report corresponding to International Application No. EP 15 18 4915.5 dated Jan. 5, 2016.
European Search Report dated Feb. 22, 2017, issued in EP Application No. 16193636.
Chinese Office Action dated Jun. 8, 2020, issued in Chinese Appln. No. 201610894039, 9 pages.

\* cited by examiner

ADAPTER ASSEMBLY FOR SURGICAL DEVICES

CROSS-REFERENCE TO RELATED APPLICATIONS

This application is a continuation of U.S. application Ser. No. 14/882,550, filed Oct. 14, 2015, the entire disclosure of which is incorporated by reference herein.

BACKGROUND

1. Technical Field

The present disclosure relates generally to powered surgical devices. More specifically, the present disclosure relates to adapter and extension assemblies for selectively connecting end effectors to actuation units of powered surgical devices.

2. Background of Related Art

Powered surgical devices for use in surgical procedures are known. To permit reuse of the handle assemblies of powered surgical devices and so that the handle assembly may be used with a variety of end effectors, adapter assemblies have been developed for selective attachment to the handle assemblies and to a variety of end effectors. Following use, the adapter may be disposed of along with the end effector. In some instances, the adapter assemblies may be sterilized for reuse.

SUMMARY

An assembly for operably connecting an end effector to a handle assembly is provided. The adapter assembly includes a coupling assembly and first, second, and third drive assemblies. The first drive assembly extends from the coupling assembly, defines a first longitudinal axis, and includes a first drive screw. The second drive assembly extends from the coupling assembly and is received about the first drive assembly. The second drive assembly defines a second longitudinal axis and includes a second drive screw in direct engagement with the first drive screw. The third drive assembly extends from the coupling assembly and is received about the first and second drive assemblies. The third drive assembly defines a third longitudinal axis and includes a third drive screw in direct engagement with the second drive screw.

In embodiments, the coupling assembly includes first, second, and third connector sleeves. The first connector sleeve may operably connect the first drive assembly to a first rotation transmitting member of a handle assembly, the second connector sleeve may operably connect the second drive assembly to a second rotation transmitting member of the handle assembly, and the third connector sleeve may operably connect the third drive assembly to a third rotation transmitting member of the handle assembly.

Each of the first, second, and third drive assemblies may include a proximal drive shaft, a distal drive shaft, and a drive screw. The first drive assembly may include a first drive screw having a threaded portion and a trocar member operably received about the threaded portion. Rotation of the first drive screw may cause longitudinal movement of the trocar member. The first, second, and third longitudinal axes may be co-axial.

The first drive assembly may further include a thrust plate. The first drive screw may engage the thrust plate during operation of the first drive assembly. Each of the first, second, and third drive assemblies may include a bearing assembly for rotatably supporting the respective first, second and third drive screws.

The adapter assembly may further include a connection assembly configured for operable connection to a handle assembly. Each of the first, second, and third drive assemblies may include a housing plate for supporting the respective first, second, and third drive screws. The first, second, and third longitudinal axes may be offset from a longitudinal axis of a handle assembly.

The adapter assembly may further include an outer sleeve. Each of the first, second, and third drive assemblies may extend through the outer sleeve. A distal end of the outer sleeve may be configured for operable connection to an end effector.

BRIEF DESCRIPTION OF THE DRAWINGS

Embodiments of the present disclosure are described herein with reference to the accompanying drawings, wherein.

DETAILED DESCRIPTION OF EMBODIMENTS

Embodiments of the presently disclosed adapter assembly for surgical devices and/or handle assemblies are described in detail with reference to the drawings, in which like reference numerals designate identical or corresponding elements in each of the several views. As used herein the term "distal" refers to that portion of the adapter assembly or surgical device, or component thereof, farther from the user, while the term "proximal" refers to that portion of the adapter assembly or surgical device, or component thereof, closer to the user.

Figures 1, 2:
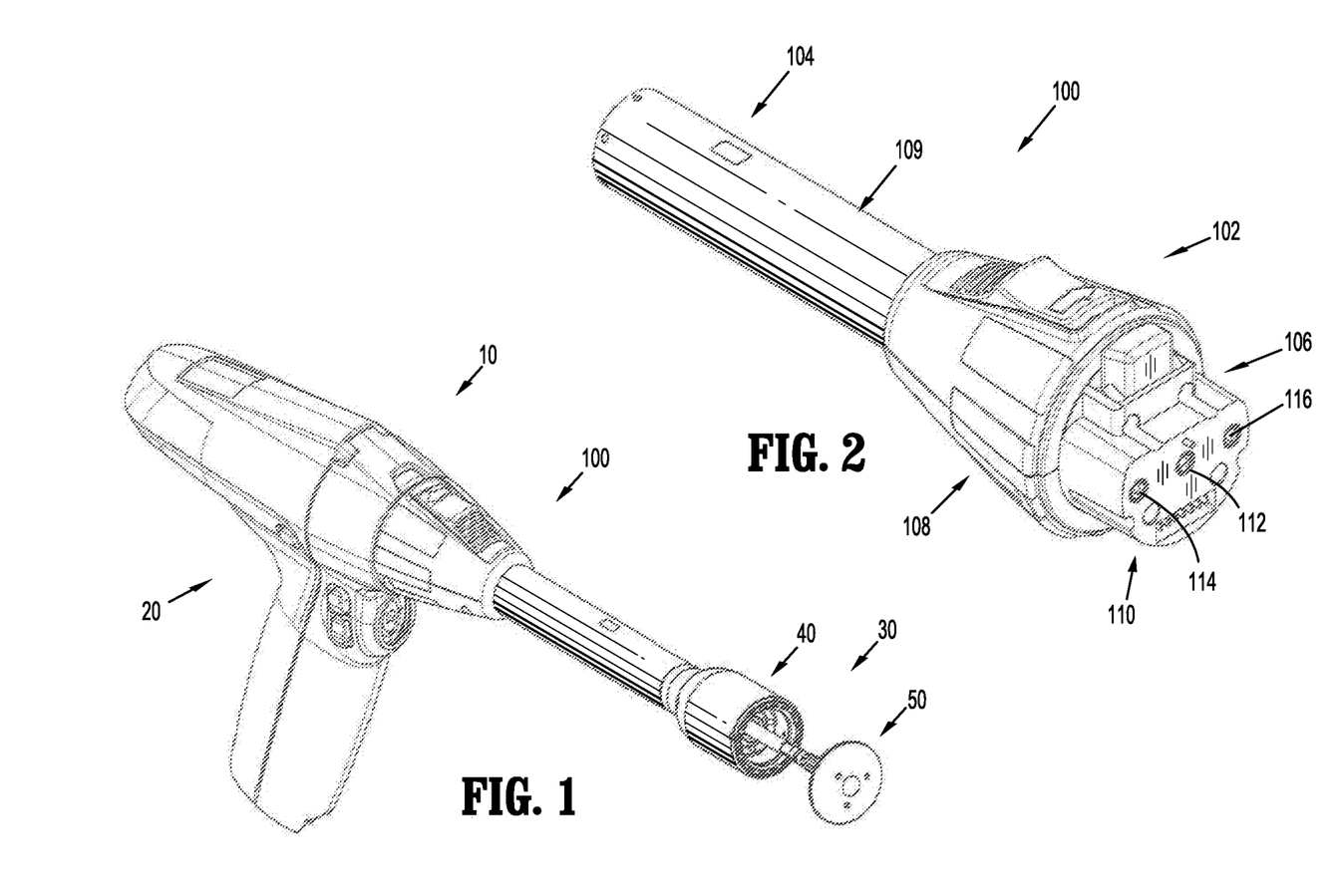
FIG. 1 is a perspective end view of an adapter assembly, in accordance with an embodiment of the present disclosure, secured to an exemplary handle assembly and with an exemplary tool assembly secured thereto.
FIG. 2 is a perspective end view of the adapter assembly of FIG. 1.

With reference to FIG. 1, an adapter assembly in accordance with an embodiment of the present disclosure, shown generally as adapter assembly 100, is configured for selective connection to a powered hand-held electromechanical actuator shown, generally as handle assembly 20. As illustrated in FIG. 1, the adapter assembly 100 is configured for selective connection with the handle assembly 20. A tool assembly or end effector, e.g. tool assembly 30, which may, in exemplary embodiments, include a loading unit 40 and an anvil assembly 50, for applying a circular array of staples (not shown) to tissue (not shown) is configured for selective connection with the adapter assembly 100. The handle assembly 20, the adapter assembly 100, and the tool assembly 30 form a surgical stapling device 10. Although shown and described for use with a circular stapling loading unit, it is envisioned that the adapter assemblies of the present disclosure may be modified for use with stapling assembly having alternative configurations, and/or with non-stapling end effectors.

For a detailed description of the structure and function of an exemplary handle assembly, please refer to commonly owned U.S. Pat. Appl. Publ. No. 2012/0253329 ("the '329 application"), the content of which is incorporated by reference herein in its entirety.

Figure 3:
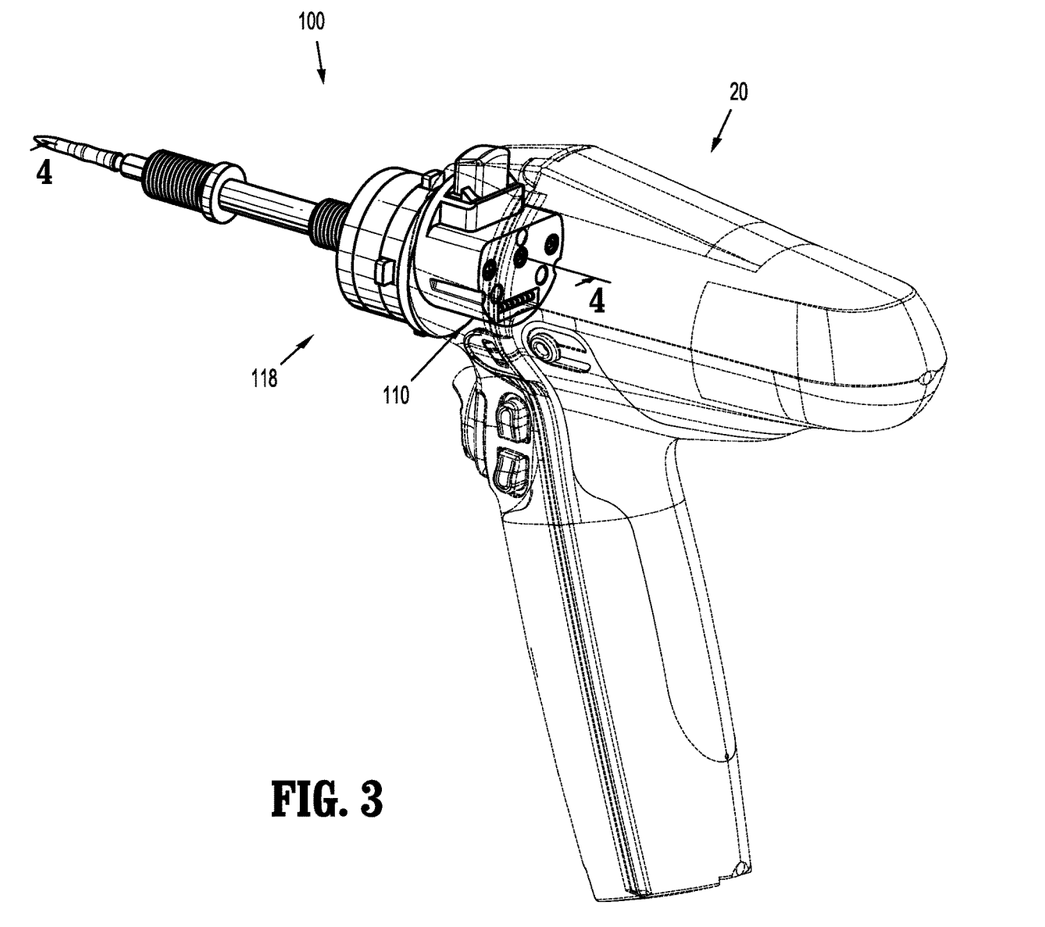
FIG. 3 is a perspective side view of the adapter assembly of FIG. 1 with a handle member and sleeve removed, and secured to the handle assembly of FIG. 1 (shown in phantom)

Referring initially to FIGS. 1-3, adapter assembly 100 includes a proximal portion 102 configured for operable connection to the handle assembly 20 (FIG. 1) and operable engagement by a user, and a distal portion 104 configured for operable connection to, and placement of, the tool assembly 30 (FIG. 1), including the loading unit 40 (FIG. 1) and the anvil assembly 50 (FIG. 1). More particularly, the proximal portion 102 of the adapter assembly 100 includes a base member 106, and a handle member 108 rotatably secured to the base member 106. The distal portion 104 includes a sleeve 109 fixedly secured to and extending from the handle member 108. A central longitudinal axis "X" (FIG. 4) of the adapter assembly 100 is offset a distance "d" (FIG. 4) from a central longitudinal axis "Y" (FIG. 4) of the handle assembly 20 (FIG. 1). In one embodiment, the offset distance "d" is approximately 0.25 inches, while in another embodiment, the offset distance "d" is approximately 0.075 inches.

The adapter assembly 100 includes a coupling assembly 110 disposed within the base member 106 of the adapter assembly 100 for operatively connecting the drive shafts (not shown) of the handle assembly 20 with a drive mechanism 118 of the adapter assembly 100. The coupling assembly 110 includes first, second, and third connector sleeves 112, 114, 116 rotatably supported within the base member 106 of the adapter assembly 100. The first, second, and third connector sleeves 112, 114, 116 of the coupling assembly 110 operably connect respective, first, second, and third drive shafts (not shown) of the handle assembly 20 (FIG. 1) with respective first, second, and third drive assemblies 120, 140, 160 of the drive mechanism 118 of the adapter assembly 100. For a more detailed description of an exemplary coupling assembly, please refer to commonly owned U.S. Provisional Patent Application Ser. No. 62/066,518, filed Oct. 21, 2014, the content of which are incorporated herein by reference in its entirety.

Figure 6:
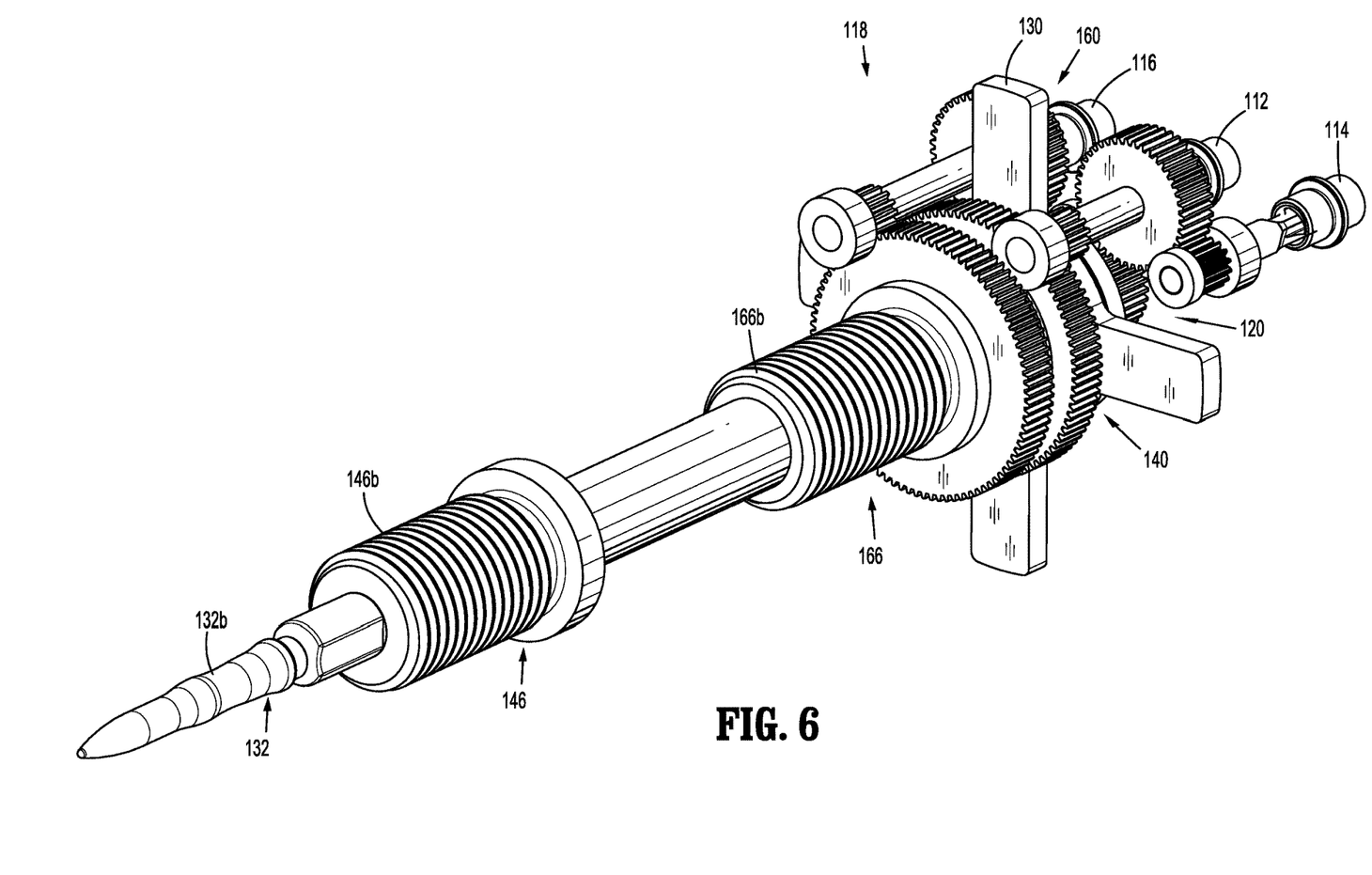
FIG. 6 is a perspective end view of a coupling assembly and a drive mechanism of the adapter assembly of FIG. 1.
Figure 7:
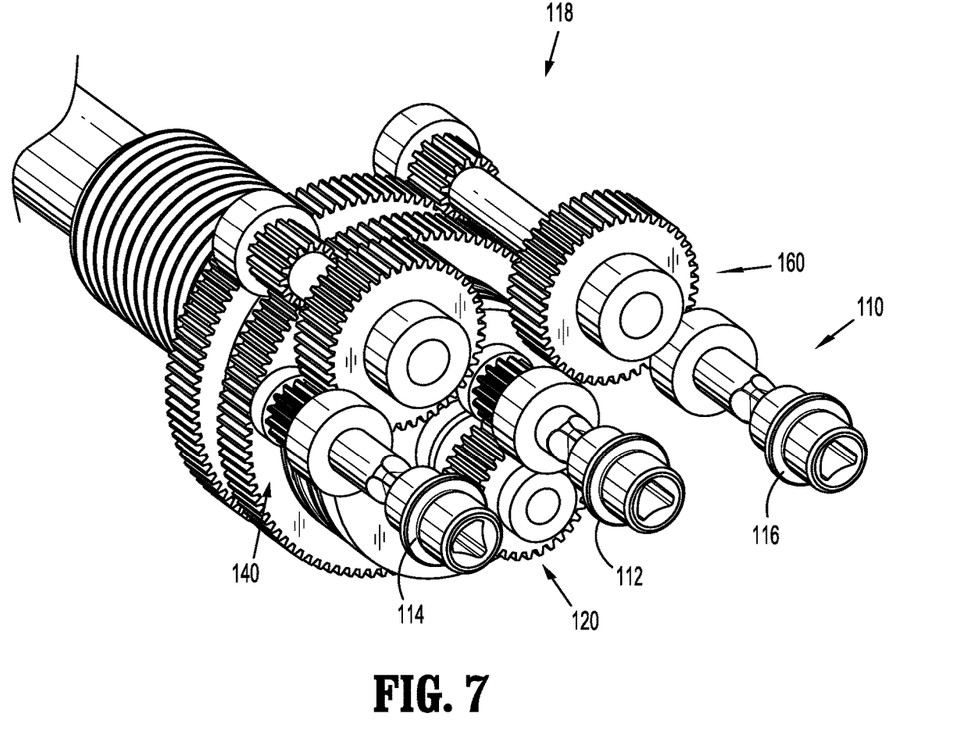
FIG. 7 is an enlarged perspective end view of the coupling assembly and the drive mechanism of FIG. 6.
Figure 8:
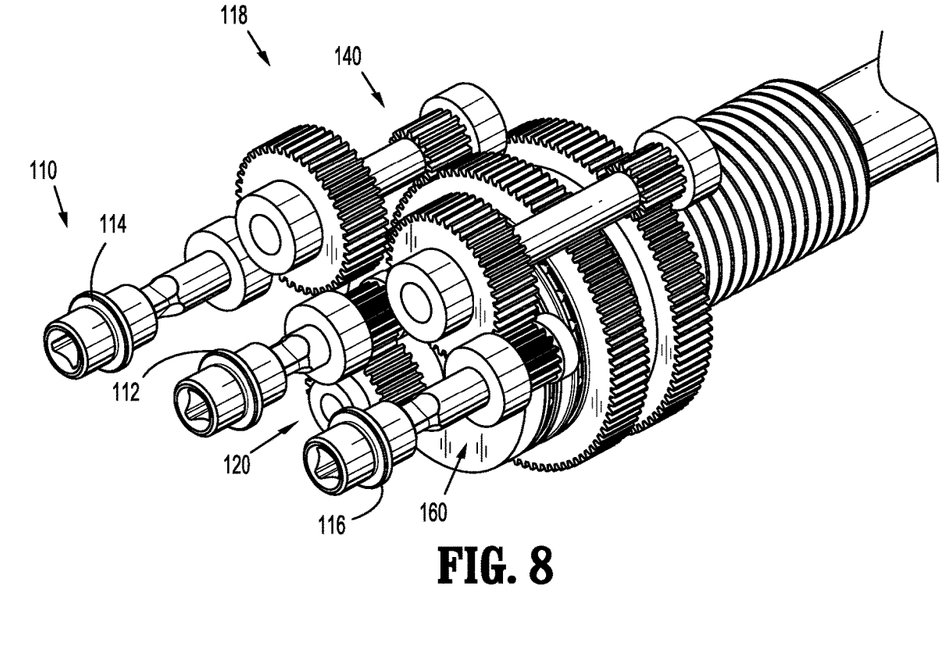
FIG. 8 is another enlarged perspective end view of the coupling assembly and the drive mechanism of FIG. 6.
Figures 9, 10:
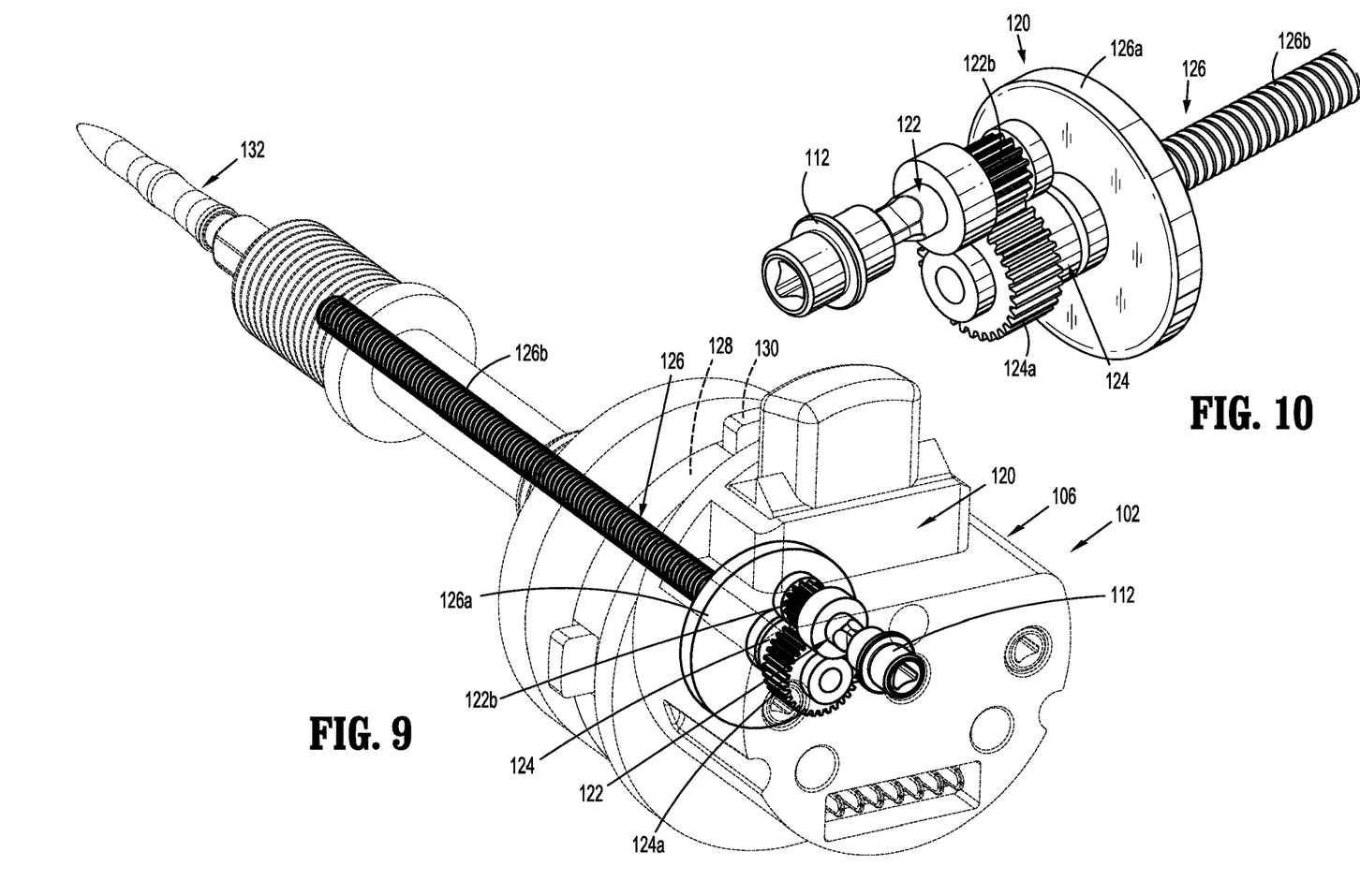
FIG. 9 is a perspective end view of a first drive assembly of the drive mechanism of FIG. 6 supported within a base member of the adapter assembly (shown in phantom)
FIG. 10 is an enlarged perspective end view of a proximal end of the first drive assembly shown in FIG. 9.

With reference now to FIGS. 9 and 10, the first drive assembly 120 of the drive mechanism 118 (FIG. 6) of the adapter assembly 100 includes a first drive shaft 122 and a first distal drive shaft 124 rotatably supported within the base member 106, and a first drive screw 126 rotatably supported between a first housing plate 128 (FIG. 9; shown in phantom) and a thrust plate 130 (FIG. 9; shown in phantom). A proximal end of the first drive shaft 122 is operably connected to the first connector sleeve 112 of the coupling assembly 110. A distal end of the first drive shaft 122 includes a first drive gear 122b integrally formed therewith, or non-rotatably supported thereon. A proximal end of the first distal drive shaft 124 includes a second drive gear 124a integrally formed therewith, or non-rotatably supported thereon, operably connected with the first drive gear 122b. A distal end of the first distal drive shaft 124 is operably connected to the first drive screw 126. Although shown as separate components, it is envisioned that the first distal drive shaft 124 and the first drive screw 126 may be monolithically formed. A proximal end of the first drive screw 126 includes a gear flange 126a integrally formed therewith, or non-rotatably supported thereon. A distal end of the first drive screw 126 includes a threaded portion 126b.

Figure 5:
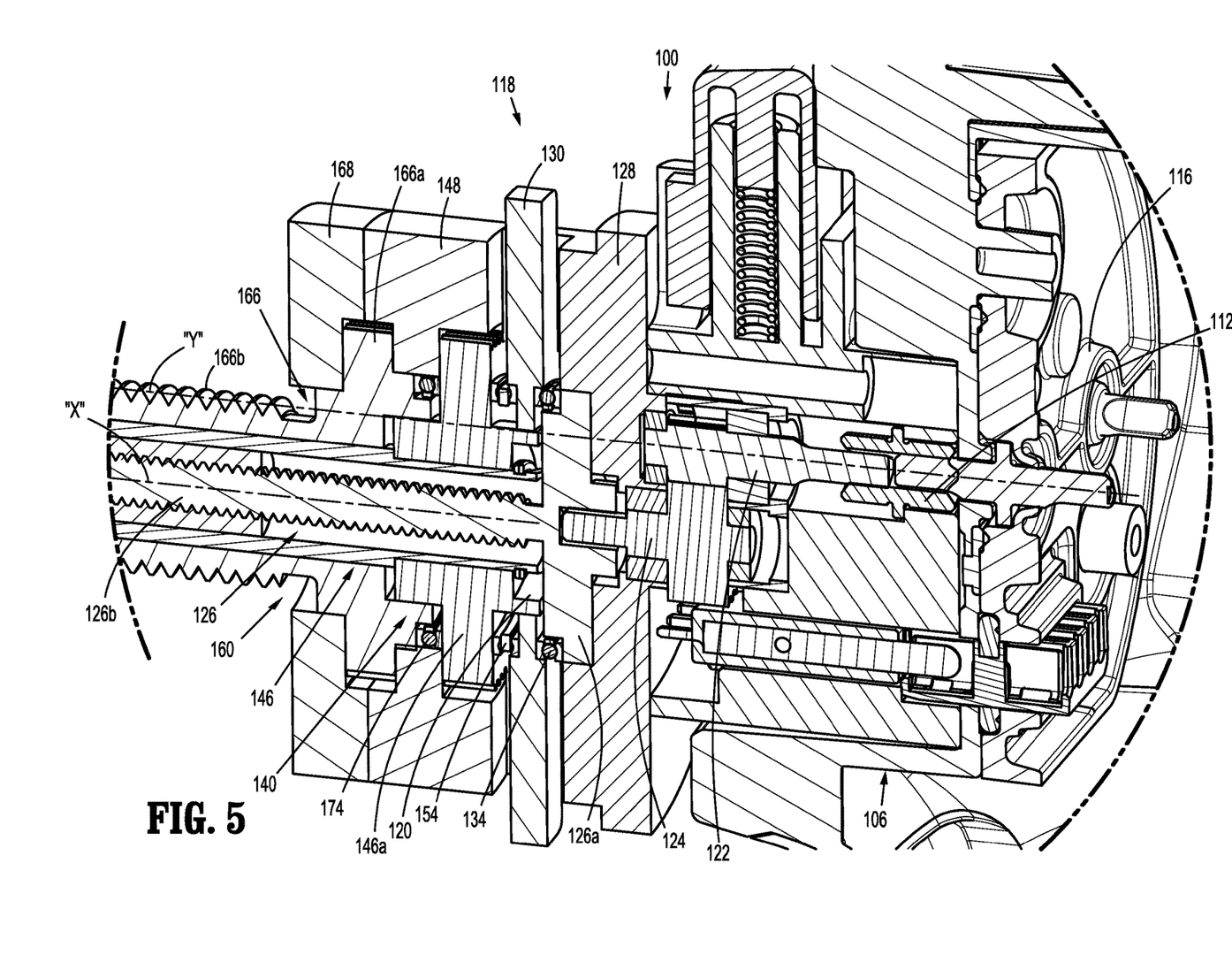
FIG. 5 is an enlarged view of the indicated area of detail of FIG. 4.

The gear flange 126a of the first drive screw 126 of the first drive assembly 120 is rotatably received between the first housing plate 128 (FIG. 9; shown in phantom) and the thrust plate 130 (FIG. 9; shown in phantom). A first bearing assembly 134 (FIG. 5) facilitates rotation of the first drive screw 126 between the first housing plate 128 and the thrust plate 130. Although not shown, the thrust plate 130 engages the handle member 108 of the adapter assembly 100 to distribute the load from the first drive assembly 120 to the handle member 108. A central longitudinal axis of the first drive screw 126 extends along the central longitudinal axis "x" of the adapter assembly 100.

Figure 4:
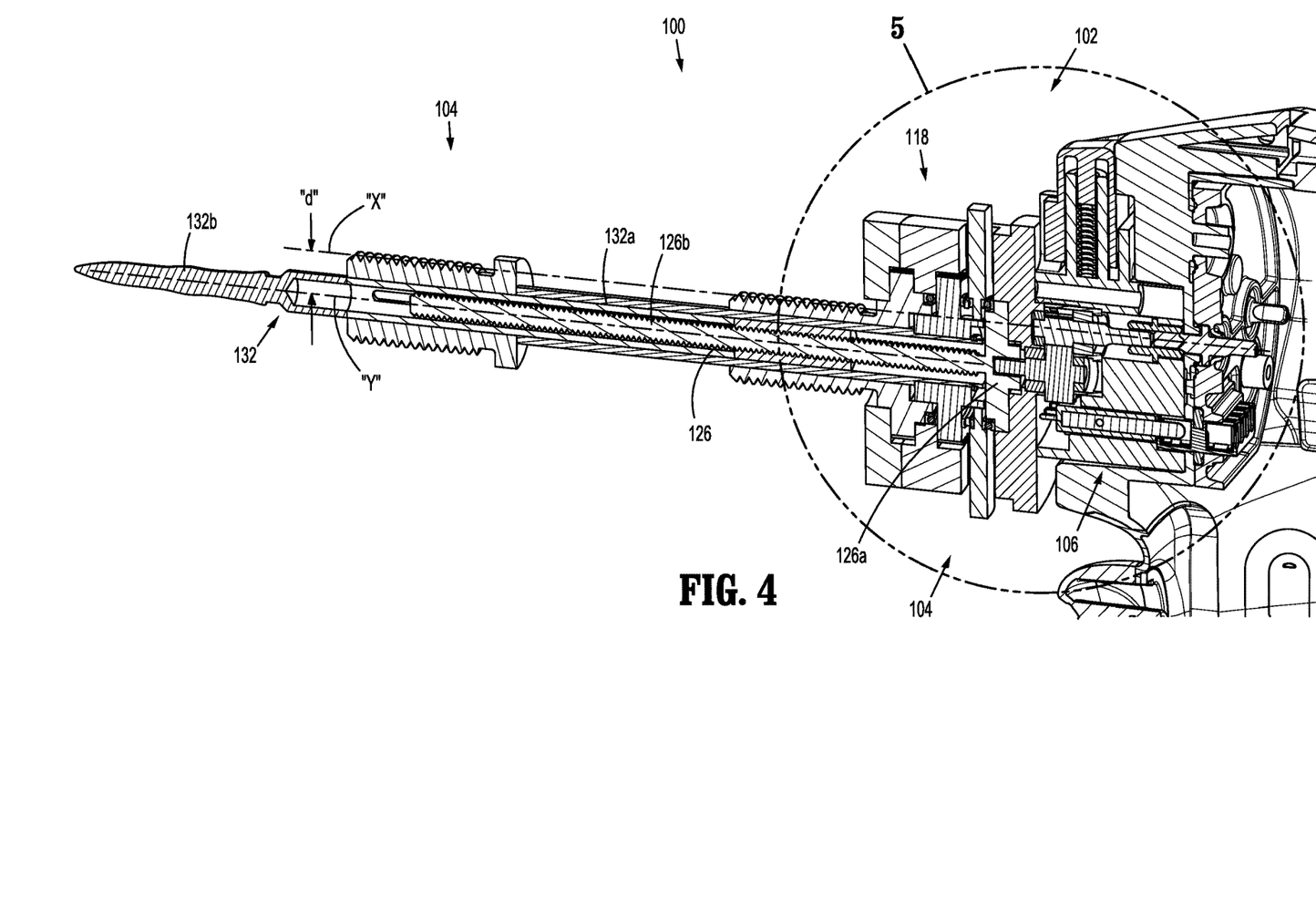
FIG. 4 is a cross-sectional side view taken along line 4-4 of FIG. 3.

As shown in FIG. 4, a threaded proximal end 132a of a trocar member 132 of the first drive assembly 120 is operably received about the threaded portion 126b of the first drive screw 126. Rotation of the first drive screw 126 about the longitudinal axis "x" effects longitudinal movement of the trocar member 132. When the anvil assembly 50 (FIG. 1) is secured to a distal end 132b of the trocar member 132, rotation of the first drive screw 126 in a first direction causes approximation of the anvil assembly 50 relative to the loading unit 40 (FIG. 1). Conversely, rotation of the first drive screw 126 in a second direction causes the anvil assembly 50 to move away from the loading unit 40. Alternatively, the first drive screw 126 operatively connects to a linearly or rotationally actuated assembly (not shown) of an end effector (not shown) for effecting performance of a first function, e.g., clamping tissue (not shown). In one embodiment, the thrust plate 130 may include a strain gauge for measuring the clamping forces during operation of the first drive assembly 120. By changing the size of the first and second drive gears 122b, 124a of the first drive assembly 120, the rate at which the drive screw 126 rotates relative to the input from the handle assembly 20 may be varied.

Figure 11:
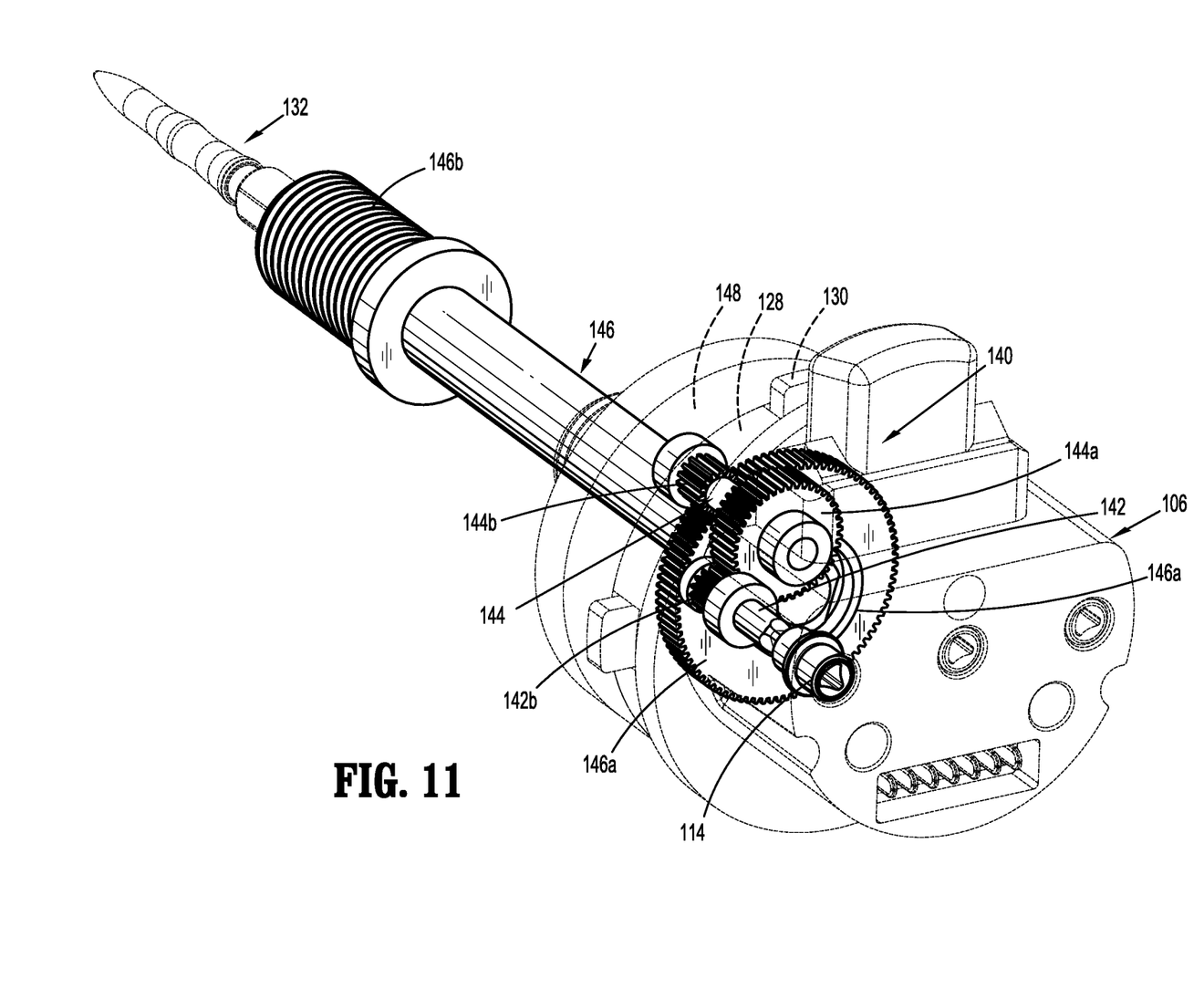
FIG. 11 is a perspective end view of a second drive assembly of the drive mechanism of FIG. 6 supported within the base member of the adapter assembly (shown in phantom)
Figure 12:
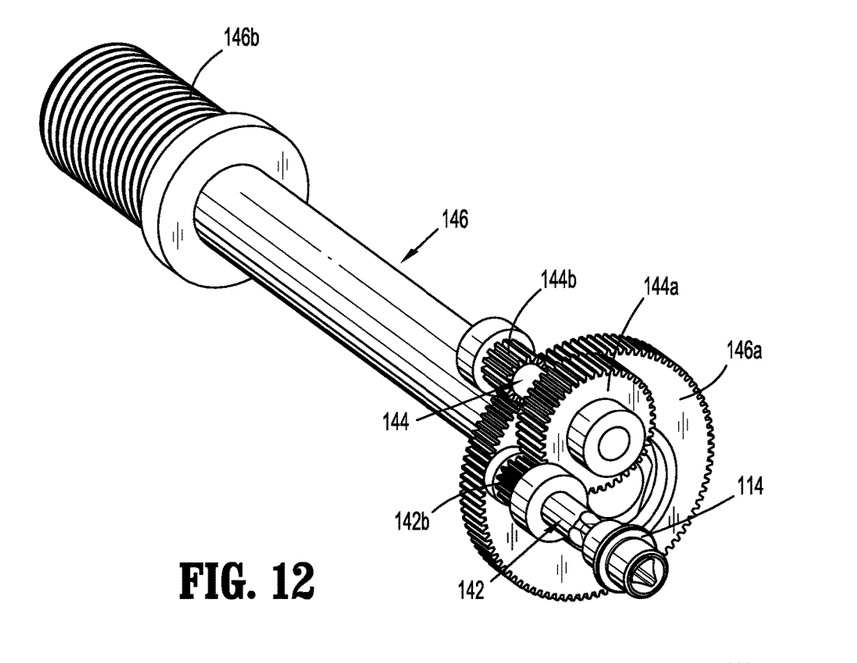
FIG. 12 is a perspective end view of the second drive assembly shown in FIG. 11.
Figure 13:
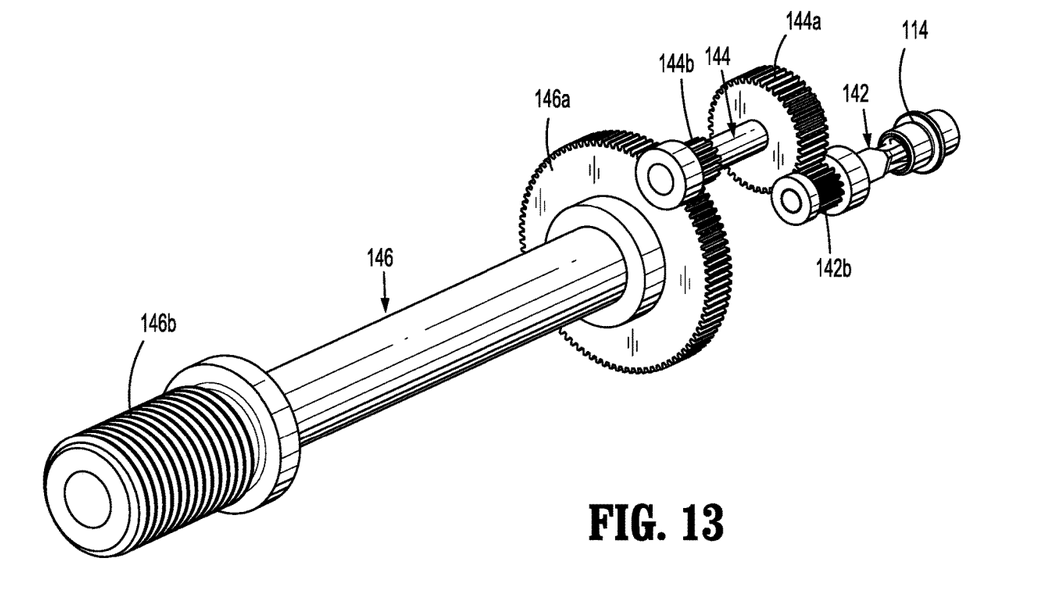
FIG. 13 is another perspective end view of the second drive assembly shown in FIG. 11.

With reference now to FIGS. 11-13, the second drive assembly 140 of the drive mechanism 118 (FIG. 6) of the adapter assembly 100 (FIG. 1) includes a second drive shaft 142 and a compound gear shaft 144 rotatably supported within the base member 106, and a second drive screw 146 rotatably supported between the gear flange 126a of the first drive screw 126 and a second housing plate 148. As will be described in further detail below, when the second drive screw 146 of the second drive assembly 140 experiences a load in the proximal direction, engagement of the second drive screw 146 with the first drive screw 126 of the first drive assembly 120 distributes the load from the second drive assembly 140 to the first drive assembly 120. This arrangement balances the load experienced in the first drive assembly 120, i.e., in the distal direction, with the load experienced in the second drive assembly 140, i.e., in the proximal direction, during operation of the adapter assembly 100.

A proximal end of the second drive shaft 142 of the second drive assembly 140 is operably connected to the second connector sleeve 114 of the coupling assembly 110. A distal end of the second drive shaft 142 includes a first drive gear 142b integrally formed therewith, or non-rotatably supported thereon. A proximal end of the compound gear shaft 144 includes a second drive gear 144a integrally formed therewith, or non-rotatably supported thereon and a distal end of the compound gear shaft 144 includes a third drive gear 144b. The second drive gear 144a is operably connected with the first drive gear 142b and the third drive gear is operably connected to the second drive screw 146. As shown, the second drive gear 144a includes a larger diameter than the third drive gear 144b. In this manner, the compound gear shaft 146 operates to reduce the output speed and increase the output torque delivered to the second drive screw 146 from the handle assembly 20. In embodiments, the second compound gear shaft 146 replaces a planetary gear system (not shown), thereby saving space within the adapter assembly 100 and reducing the number of gears necessary for the operation of the adapter assembly 100.

A proximal end of the second drive screw 146 includes a gear flange 146a integrally formed therewith, or non-rotatably supported thereon, in operable engagement with the third drive gear 144b of the compound gear shaft 144. A distal end of the second drive screw 146 includes a threaded portion 146b. The second drive screw 146 of the second drive assembly 140 is received about the threaded portion 126b of the first drive screw 126 of the first drive assembly 120 and accommodates receipt of the trocar member 132 of the first drive assembly 120 about the threaded portion 126a of the first drive screw 126.

The gear flange 146a of the second drive screw 146 of the second drive assembly 140 is rotatably received between the gear flange 126a of the first drive screw 126 and the second housing plate 148. A second bearing assembly 154 facilitates rotation of the second drive screw 146 between the gear flange 126a of the first drive screw 126 and the second housing plate 148. A central longitudinal axis of the second drive screw 146 extends along the central longitudinal axis "x" (FIG. 4) of the adapter assembly 100.

The threaded portion 146b of the second drive screw 146 operably connects to a linearly or rotationally actuated assembly (not shown) of the loading unit 40 (FIG. 1) of the tool assembly 30 (FIG. 1), or other suitable end effector, for effecting performance of a second function, e.g., stapling tissue (not shown).

Figures 14, 15:
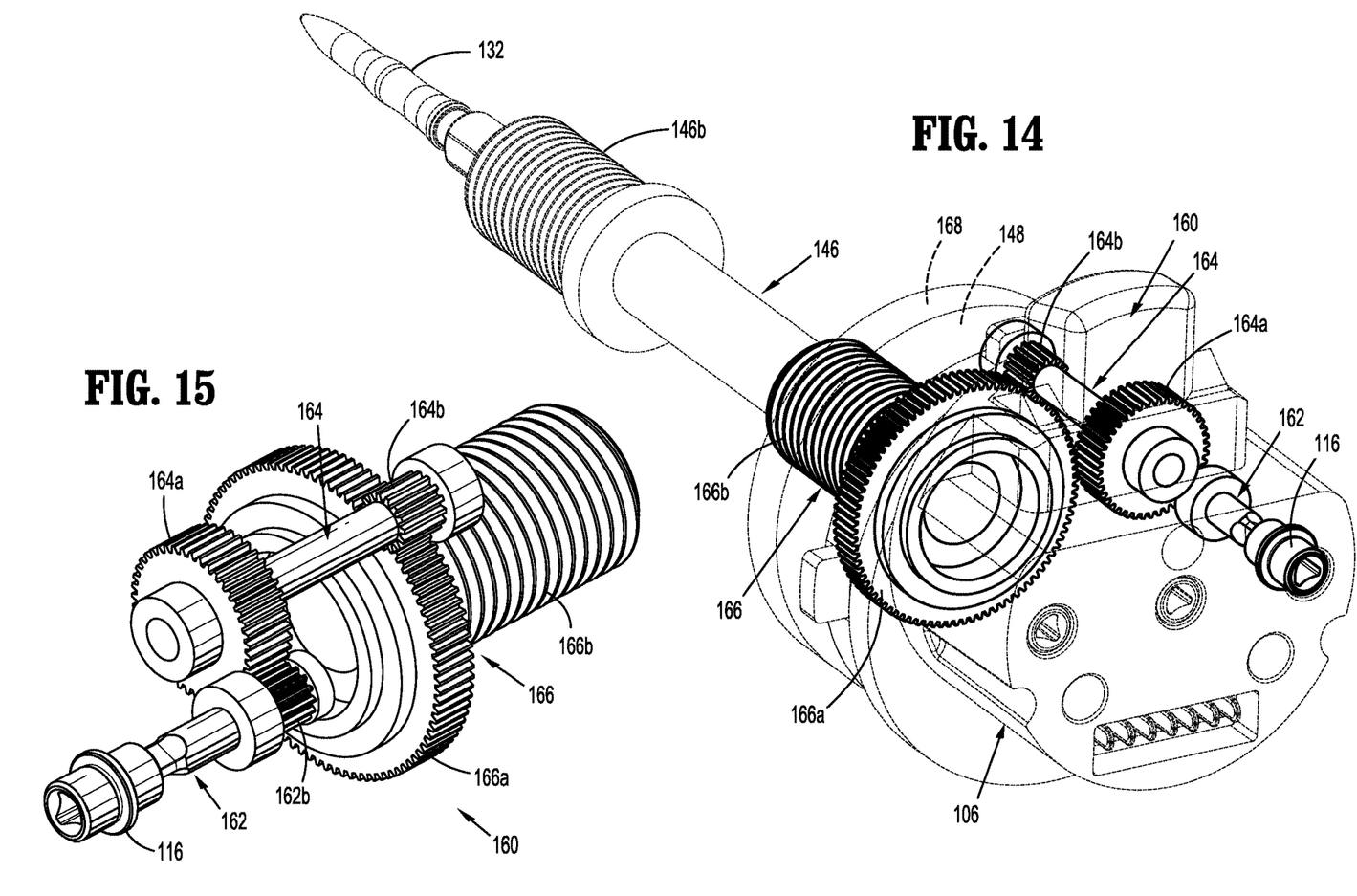
FIG. 14 is a perspective end view of a third drive assembly of the drive mechanism of FIG. 6 supported within the base member of the adapter assembly (shown in phantom)
FIG. 15 is a perspective end view of the third drive assembly shown in FIG. 14.

With reference now to FIGS. 14 and 15, the third drive assembly 160 of the drive mechanism 118 of the adapter assembly 100 includes a third drive shaft 162 and a compound gear shaft 164 rotatably supported within the base member 106, and a third drive screw 166 rotatably supported between the gear flange 146a of the second drive screw 146 and a third housing plate 168. As will be described in further detail below, when the third drive screw 166 of the third drive assembly 160 experiences a load in the proximal direction, engagement of the third drive screw 166 of the third drive assembly 160 with the second drive screw 146 of the second drive assembly 140, and engagement of the second drive screw 146 of the second drive assembly 140 with the first drive screw 126 of the first drive assembly 120, distributes the loads from the second and third drive assemblies 140, 160 to the first drive assembly 120. This arrangement balances the load experienced in the first drive assembly 120, i.e., in the distal direction, with the loads experienced in the second and third drive assemblies 140, 160, i.e., in the proximal direction, during operation of the adapter assembly 100.

A proximal end of the third drive shaft 162 of the third drive assembly 160 operably engages the third connector sleeve 116 of the coupling assembly 110. A distal end of the third drive shaft 162 includes a first drive gear 162b integrally formed therewith, or non-rotatably supported thereon. A proximal end of the compound gear shaft 164 includes a second drive gear 164a integrally formed therewith, or non-rotatably supported thereon, and a distal end of the compound gear shaft 164 includes a third drive gear 164b. The second drive gear 164a is operably connected with the first drive gear 162b and the third drive gear is operably connected to the second drive screw 166. As shown, the second drive gear 164a includes a larger diameter than the third drive gear 164b. In this manner, the compound gear shaft 164 operates to reduce the output speed and increase the output torque delivered to the third drive screw 166 from the handle assembly 20. In embodiments, the third compound gear shaft 164 replaces a planetary gear system (not shown) used in previous embodiments, thereby saving space within the adapter assembly 100 and reducing the number of gears necessary for the operation of the adapter assembly 100.

A proximal end of the third drive screw 166 includes a gear flange 166a integrally formed therewith, or non-rotatably supported thereon, in operable engagement with the third drive gear 164b of the compound gear shaft 164. A distal end of the third drive screw 166 includes a threaded portion 166b. The third drive screw 166 of the third drive assembly 160 is received about the second drive screw 146 of the second drive assembly 140 between the gear flange 146a of the second drive screw 146 and the threaded portion 146b of the second drive screw 146.

The gear flange 166a of the third drive screw 166 of the third drive assembly 160 is rotatably received between the gear flange 146a of the second drive screw 146 of the second drive assembly 140 and the third housing plate 168. A third bearing assembly 174 facilitates rotation of the third drive screw 166 of the third drive assembly 160 between the second flange 146a of the second drive screw 146 of the second drive assembly 140 and the third housing plate 168. A central longitudinal axis of the third drive screw 166 extends along the central longitudinal axis "x" of the adapter assembly 100. Accordingly, each of the central longitudinal axes of the first, second, and third drive assemblies 120, 140, 160 of the drive mechanism 118 extend along the central longitudinal axis "x" (FIG. 4) of the adapter assembly 100, i.e., the first second, and third drive screws 126, 146, 166 of the respective first, second, and third drive assemblies 120, 140, 160 are coaxial. In this manner, an end effector attached to the distal portion 104 of the adapter assembly 100 may be rotated about the central longitudinal axis "x" to facilitate rotational positioning of the end effector.

The threaded portion 166b of the third drive screw 166 of the third drive assembly 160 operably connects to a linearly or rotationally actuated assembly (not shown) of the loading unit 40 (FIG. 1) of the tool assembly 30 (FIG. 1), or other suitable end effector, for effecting performance of a third function, e.g., cutting tissue (not shown).

The operation of adapter assembly 100 will now be described with reference to the figures. The adapter assembly 100 is secured to the handle assembly 20 (FIG. 1) and loading unit 40 of the tool assembly 30 (FIG. 1) is secured to the adapter assembly 100 in a traditional manner. Subsequent to placement of the anvil assembly 50 (FIG. 1) of the tool assembly 30 (FIG. 1) through tissue to be stapled (not shown) and/or the placement of the tissue to be stapled around the anvil assembly 50, e.g., with a purse-string suture, the anvil assembly 50 is secured to the trocar member 132 of the adapter assembly 100.

The handle assembly 20 may then be actuated to cause individual or simultaneous rotation of any of the first, second, and third drive shafts (not shown) of the handle assembly 20 to effect actuation of the respective first, second, and third drive assemblies 120, 140, 160 of the drive mechanism 118 of the adapter assembly 100.

Referring briefly to FIGS. 9 and 10, during actuation of the handle assembly 20 (FIG. 1) to actuate the first drive assembly 120, rotation of the first drive shaft (not shown) of the handle assembly 20 rotates the first connector sleeve 112, which rotates the first drive shaft 122, which rotates the first distal drive shaft 124 to cause rotation of the first drive screw 126. Rotation of the first drive screw 126 in the first direction causes longitudinal movement of the trocar member 132 in the proximal direction, i.e., retraction, and rotation of the first drive screw 126 in the second direction causes longitudinal movement of the trocar member 132 in the distal direction, i.e., advancement.

As noted above, during actuation of the first drive assembly 120 of the drive mechanism 118, the gear flange 126a of the first drive screw 126 engages the thrust plate 130. The configuration of the adapter assembly 100 is such that the thrust plate 130 only experiences load during actuation of the first drive assembly 120. In this manner, the adapter assembly 100 will have better resolution during operation than an adapter assembly (not shown) in which the thrust plate 130 experiences additional loads from the second and third drive assemblies 140, 160. As noted above, the thrust plate 130 may include a strain gauge for measuring the clamping forces during operation of the first drive assembly 120.

Turning to FIGS. 11-13, during actuation of handle assembly 20 (FIG. 1) to actuate the second drive assembly 140, rotation of the second drive shaft (not shown) of handle assembly 20 rotates the second connector sleeve 114, which rotates the second drive shaft 142, which rotates the compound gear shaft 144 to cause rotation of the second drive screw 146. Rotation of the second drive screw 146 in the first direction causes longitudinal movement of an attached first pusher member (not shown) in a distal direction, i.e., advancement, and rotation of the second drive screw 146 in the second direction causes longitudinal movement of the attached pusher member (not shown) in a proximal direction, i.e., retraction. As noted above, during actuation of the second drive assembly 140 of the drive mechanism 118, the gear flange 146a of the second drive screw 146 engages the gear flange 126a of the first drive screw 126.

Turning to FIGS. 14 and 15, during actuation of handle assembly 20 (FIG. 1) to actuate the third drive assembly 160, rotation of the third drive shaft (not shown) of handle assembly 20 rotates the third connector sleeve 116, which rotates the third drive shaft 162, which rotates the compound gear shaft 164 to cause rotation of the third drive screw 166. Rotation of the third drive screw 166 in the first direction causes longitudinal movement of an attached second pusher member (not shown) in a distal direction, i.e., advancement, and rotation of the third drive screw 166 in the second direction causes longitudinal movement of the attached pusher member (not shown) in a proximal direction, i.e., retraction. As noted above, during actuation of the third drive assembly 160 of the drive mechanism 118, the gear flange 166a of the third drive screw 166 engages the gear flange 146a of the second drive screw 146 which engages the gear flange 126a of the first drive screw 126.

The axial load path of the adapter assembly 100 extends through the first, second, and third drive screws 126, 146, 166 of the respective first, second, and third drive assemblies 120, 140, 160. In this manner, the sleeve 109 of the adapter assembly does not experience loads from the second and third drive assemblies 140, 160. As noted above, the common central longitudinal axis of the first, second, and third drive assemblies 120, 140, 160 allows the sleeve 109 of the adapter assembly 100 to be rotated along the longitudinal axis "x" of the adapter assembly 100.

Any of the components described herein may be fabricated from either metals, plastics, resins, composites or the like taking into consideration strength, durability, wearability, weight, resistance to corrosion, ease of manufacturing, cost of manufacturing, and the like.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. An adapter assembly for operably connecting a surgical end effector to a handle assembly, the adapter assembly comprising:
   a coupling assembly;
   a first drive assembly extending from the coupling assembly, the first drive assembly including a first drive screw and a trocar member selectively extendable relative to the first drive screw;
   a second drive assembly extending from the coupling assembly and at least partially disposed about the first drive assembly, the second drive assembly including a second drive screw; and
   a third drive assembly extending from the coupling assembly and at least partially disposed about the first and second drive assemblies, the third drive assembly including a third drive screw.

2. The adapter assembly of claim 1, wherein the first drive screw defines a first longitudinal axis, the second drive screw defines a second longitudinal axis, and the third drive screw defines a third longitudinal axis, wherein at least two of the first, second, and third longitudinal axes are co-axial.

3. The adapter assembly of claim 2, wherein the first, second, and third longitudinal axes are co-axial.

4. The adapter assembly of claim 1, wherein the third drive screw is disposed proximal of the second drive screw.

5. The adapter assembly of claim 1, wherein the trocar member is slidably disposed through the second drive screw.

6. The adapter assembly of claim 1, wherein the coupling assembly includes first, second, and third connector sleeves.

7. The adapter assembly of claim 6, wherein the first connector sleeve operably connects the first drive assembly to a first rotation transmitting member of a handle assembly, the second connector sleeve operably connects the second drive assembly to a second rotation transmitting member of the handle assembly, and the third connector sleeve operably connects the third drive assembly to a third rotation transmitting member of the handle assembly.

8. The adapter assembly of claim 1, wherein each of the first, second, and third drive assemblies further include a proximal drive shaft and a distal drive shaft.

9. The adapter assembly of claim 1, wherein the first drive screw includes a threaded portion and the trocar member is operably received about the threaded portion.

10. The adapter assembly of claim 1, wherein rotation of the first drive screw causes longitudinal movement of the trocar member.

11. The adapter assembly of claim 1, wherein the first drive assembly further includes a thrust plate, the first drive screw engaging the thrust plate during operation of the first drive assembly.

12. The adapter assembly of claim 1, wherein each of the first, second, and third drive assemblies includes a bearing assembly for rotatably supporting the respective first, second, and third drive screws.

13. The adapter assembly of claim 1, further including a connection assembly configured for operable connection to a handle assembly.

14. The adapter assembly of claim 1, wherein each of the first, second, and third drive assemblies includes a housing plate for supporting the respective first, second, and third drive screws.

15. The adapter assembly of claim 1, wherein the first, second, and third longitudinal axes are offset from a longitudinal axis of a handle assembly.

16. The adapter assembly of claim 1, further including an outer sleeve, wherein each of the first, second, and third drive assemblies extends at least partially through the outer sleeve.

17. The adapter assembly of claim 16, wherein a distal end of the outer sleeve is configured for operable connection to the surgical end effector.

* * * * *